US00PP09095P

United States Patent [19]

McGredy

[11] Patent Number: Plant 9,095

[45] Date of Patent: Apr. 4, 1995

[54] GRANDIFLORA ROSE PLANT NAMED MACMOUHOO

[75] Inventor: Sam McGredy, Auckland, New Zealand

[73] Assignee: Certified Roses, Inc., Tyler, Tex.

[21] Appl. No.: 243,497

[22] Filed: May 16, 1994

[51] Int. Cl.[6] ..... A01H 5/00

[52] U.S. Cl. ..... Plt./15

[58] Field of Search ..... Plt. 14, 15, 23, 24

*Primary Examiner*—Howard J. Locker

*Attorney, Agent, or Firm*—Christie, Parker & Hale

[57] ABSTRACT

A new grandiflora rose plant producing near white flowers.

1 Drawing Sheet

SUMMARY OF THE INVENTION

The present invention raltes to a new and distinct variety of rose plant of the grandiflora rose class which has as its seed parent the vareity known as 'Sexy Rexy' U.S. Plant Pat. No. 6,713, and as pollen point the variety known as 'Pot O' Gold.' The varietal denomination of this new rose is 'Macmouhoo.'

Among the novel characteristics possessed by this new variety which distinguish it from its parent and all other varieties of which I am aware are its attractive near white flowers of hybrid tea quality produced in well-spaced clusters on a tall, free breaking plant.

Asexual reproduction by budding of the new vareity as performed in Auckland, New Zealand shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new vareity in different stages of development and depicted in color as nearly true as it is reasonably possible to maek the same in a color illustration of this character.

DETAILED DESCRIPTION OF THE NEW VARIETY

Parentage: Seedling.

*Seed parent.*—'Sexy Rexy'.

*Pollen parent.*—'Pot O'Gold'.

Class: Grandiflora.

The following is a detailed description of my new variety, of specimens grown outdoors in Auckland, New Zealand in the month of February. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Recurrent.

A. Bud:

(1) *Size.*—Medium, about one inch long by one inch wide, depending on the time of the year and the temperature.

(2) *Form.*—Ovoid.

(3) *Color.*—When sepals first divide, bud color is near 11C.

(4) *Sepals.*—Longer than bud, pointed, near 144B on outside; near 147D on reverse.

(5) *Peduncle.*—Length: About 4 cm. Aspect: Usually upright sometimes slightly pendulous. Strength: Erect. Color: Near 144C.

B. Bloom:

(1) *Size.*—Average size when fully expanded — about 9 cm.

(2) *Borne.*—In sprays of 6–10 bloom.

(3) *Form.*—Ovoid at first, opening flat while retaining form. Fully open bloom has a few small center petals in addition to petaloids.

(4) *Petalage.*—Number of petals under normal conditions — about 48.

(5) *Color.*—($\frac{1}{3}$ to $\frac{1}{2}$ open): Outer petals: Top Surface: Near 4D. Undersurface: Near 4D. Inner petals: Top Surface: Near 4C. Undersurface: Near 4C. Base of petals: (point of attachment): Near 4A. General tonality from a distance: Cream.

(6) *Color (fully open).*—Outer Petals: Top surface: Cream, shading to near 4D towards the center. Undersurface: Near 4C. Inner petals: Top surface: Near 4D. Undersurface: Near 4D. Base of petals: (point of attachment): Near 4A. General tonality from a distance: Cream.

(7) *Color change.*—As bloom ages there is little color change. Petal: Top surface: Very little from near 4C to near 4D. Undersurface: Very little from near 4C to near 4D. General tonality at a distance: Cream.

C. Petals:

(1) *Texture.*—Thick, firm.

(2) *Appearance.*—Matte but velvety to touch on top surface.

(3) *Form*—Ovoid.

(4) *Arrangement.*—Imbricated.

(5) *Petaloids.*—Many, 8 to 10.

(6) *Fragrance.*—Medium old rose fragrance.

(7) *Lasting quality.*—Moderately long lasting, up to six to seven days on the plant but does not last well as a cut flower.

(8) *Persistence.*—Drop off cleanly.

REPRODUCTIVE ORGANS

A. Stamens:

(1) *Arrangement.*—Irregularly arranged, varying length.

(2) *Pollen.*—Color — near 23A.

B. Pistils:

(1) *Styles.*—Bunched, uneven, medium length.

(2) *Stigmas.*—Color — near 20C.

C. Characteristics of hips: Urn shaped, 1-1.5 cm, orange scarlet at maturity, seeds do not protrude.

PLANT

A. Form: Upright, tall.

B. Growth: Very vigorous; height attained about 1.25 meters at first season.

C. Foliage: Usually compound 7, sometime 3 and 5, leaflets.

(1) *Size.*—Medium.

(2) *Quantity.*—Very abundant.

(3) *Color.*—New foliage: Upper side — purple to near 152A. Underside — near 152A shaded red near 47B. Old foliage Upper side—near 137A. 137A. Underside — near 147C.

(4) *Shape.*—Long pointed.

(5) *Texture.*—Shiny smooth top, matte rough underside.

(6) *Edge.*—Serrated.

(7) *Serration.*—Denticulate.

(8) *Leaf stem.*—Color — near 143A top, near 143C underside.

(9) *Stipules.*—Medium.

(10) *Resistance to disease.*—Good resistance to blackspot; very good resistance to mildew and rust.

D. Wood (1) *New wood.*—Color — new shoots near 144C; Bark very smooth.

(2) *Old wood.*—Color — near 144D. Bark — smooth.

E. Flower stem: About 45-60 cm from last cut.

F. Thorns:

*Quantity* (*main stalk*).—Ordinary.

*On laterals from stalk.*—Average.

*Form.*—Curved downward, wide at base.

*Length.*—Medium.

*Color.*—Near 22C, lightly shaded near 46D.

*Position.*—Regular.

*Prickles.*—Some.

F. Winter hardiness: Winter hardy in New Zealand and in Texas.

I claim:

1. A new and distinct variety of rose plant of the grandiflora rose class, substantially as shown and described.

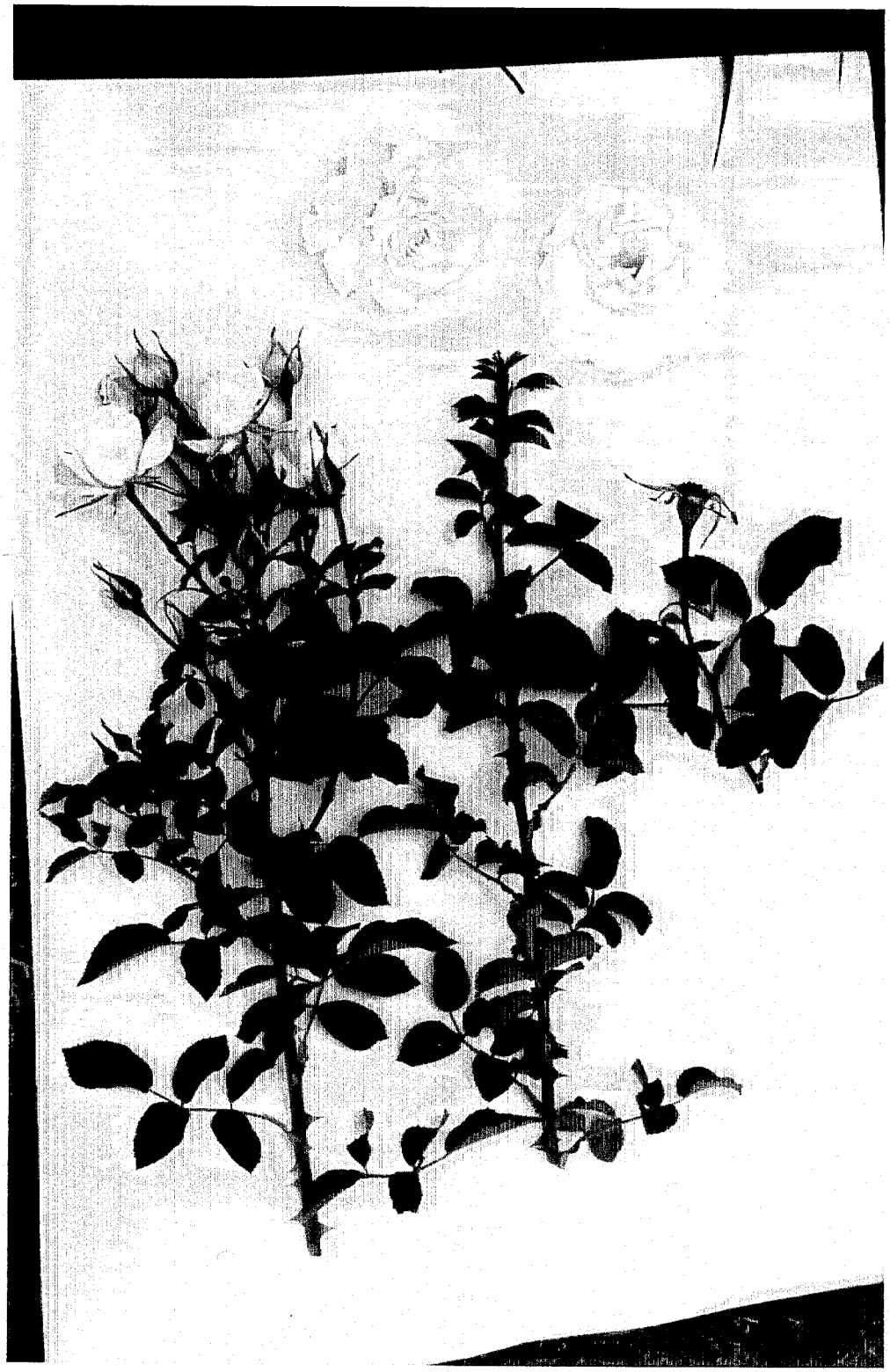

* * * * *